United States Patent [19]

Grisar et al.

[11] 4,281,006
[45] Jul. 28, 1981

[54] 2-(DIPHENYLALKYLIMINO)PIPERIDINE-3-CARBOXANILIDES AS INHIBITORS OF GASTROINTESTINAL HYPERSECRETION

[75] Inventors: J. Martin Grisar; Norbert L. Wiech, both of Cincinnati, Ohio

[73] Assignee: Richardson-Merrell Inc., Wilton, Conn.

[21] Appl. No.: 146,132

[22] Filed: May 2, 1980

[51] Int. Cl.³ .................. A61K 31/445; C07D 211/60
[52] U.S. Cl. ..................... 424/267; 424/266; 546/224; 546/291; 546/309
[58] Field of Search .............. 546/224, 309; 424/266, 424/267

[56] References Cited

U.S. PATENT DOCUMENTS

| | | | |
|---|---|---|---|
| 3,725,435 | 4/1973 | Poos | 260/326.85 |
| 3,783,162 | 6/1974 | Grisar et al. | 424/267 |
| 3,963,701 | 6/1976 | Grisar et al. | 424/244 X |
| 4,061,746 | 12/1977 | Blohm et al. | 424/244 |

OTHER PUBLICATIONS

Grisar, J., et al., *J. Med. Chem.*, 1973, 16(8), 885–893.
Benson, R., et al., *J. Am. Chem. Soc.*, 70, 2115–2118 (1948).
Aldrich Chemical Co., Catalog 20 (1980), pp. 163, 165, 237, 208, 132, 133, 303, 304, 312, 313, 314, 315, 319, 327, 334, 335, 344, 345, 351, 352, 364, 365, 376, 377, 378, 908, 909, 911, 921, 926, 927, 928, 930 and 931.

*Primary Examiner*—Richard A. Schwartz
*Attorney, Agent, or Firm*—Millen & White

[57] ABSTRACT

Compounds having the formula

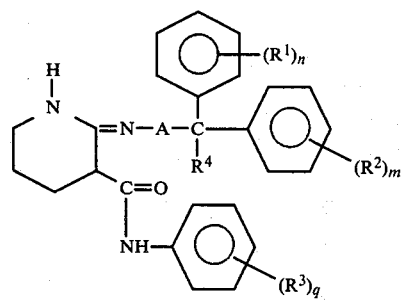

wherein A is a bond or $C_{1-4}$ alkylene; $R^1$, $R^2$ and $R^3$ are independently a halogen atom, $C_{1-4}$ alkyl, $C_{1-4}$ alkoxy, $C_{1-4}$ alkylthio, $CF_3$, $SCF_3$ or $OCF_3$; $R^4$ is a hydrogen atom or $C_{1-4}$ alkyl; and n, m and q are independently an integer from 0 to 3; and pharmaceutically acceptable acid addition salts thereof, are useful for the treatment of gastrointestinal hypersecretion.

27 Claims, No Drawings

2-(DIPHENYLALKYLIMINO)PIPERIDINE-3-CARBOXANILIDES AS INHIBITORS OF GASTROINTESTINAL HYPERSECRETION

FIELD OF THE INVENTION

The present invention relates to 2-(diphenylalkylimino)piperidine-3-carboxanilides, which are useful as inhibitors of gastrointestinal hypersecretion.

DESCRIPTION OF THE PRIOR ART

It is known that certain lactamimide derivatives may be used in the treatment of gastrointestinal hypersecretion. U.S. Pat. No. 4,061,746 discloses a variety of compounds which are effective for that use. While this reference discloses a wide range of substituents on both nitrogen atoms of the lactamimide function, none of the other carbon atoms of the lactam ring is substituted.

SUMMARY OF THE INVENTION

The compounds of the present invention, which are useful in a method of treatment of gastrointestinal hypersecretion, have the Formula I

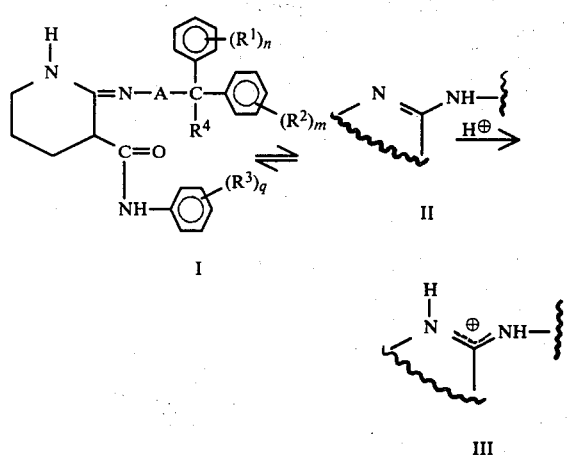

wherein A is a bond or $C_{1-4}$ alkylene; $R^1$, $R^2$ and $R^3$ are independently a halogen atom, $C_{1-4}$ alkyl, $C_{1-4}$ alkoxy, $C_{1-4}$ alkylthio, $CF_3$, $SCF_3$ or $OCF_3$; $R^4$ is a hydrogen atom or $C_{1-4}$ alkyl; and n, m and q are independently an integer from 0 to 3; and pharmaceutically acceptable acid addition salts thereof. Pharmaceutical compositions comprising these compounds, as well as a method of using them and a process for synthesizing them, are also within the scope of the present invention.

DETAILED DESCRIPTION OF THE INVENTION

The compounds of the present invention belong to the class of compounds known generally as lactamimides. Such compounds are capable of existence in either of two tautomeric forms, represented by Formulas I and II above. This tautomerism has been studied by R. Kwok and P. Pranc, *J. Org. Chem.*, 32, 740 (1967).

Acid addition salts of either tautomer are likely to have the structure represented by Formula III, where the positive charge is delocalized. In solution, under the conditions of therapeutic utility, the proportions of each tautomeric form or of the acid addition salt will be dependent upon numerous factors, including the nature of the substituents and the pH of the medium. The compounds of the invention are inherently chiral, and may also exhibit geometric isomerism about the imine double bond. Thus, the compounds of the invention should be understood to embrace compounds having structures represented by Formula I and/or Formula II and/or Formula III, either as a single, pure enantiomer or as a mixture, including a racemic mixture, of stereoisomers. For convenience, they are referred to hereinafter as compounds of Formula I.

Preferred embodiments of the compounds of the invention include those where A is a bond or a methylene group. Especially preferred are compounds wherein A is a bond and $R^4$ is H or methyl, and compounds wherein A is a methylene group and $R^4$ is H or n-propyl. Other preferred embodiments are compounds where q is 1 and $R^3$ is o-$OCH_3$ or m-$CF_3$, and compounds where n and m are 1 and $R^1$ and $R^2$ are individually a chlorine atom or a $CF_3$ group. Additional preferred embodiments are illustrated in the Examples set forth hereinbelow.

The invention also includes the pharmaceutically acceptable acid addition salts of the compounds of the hereinbefore set forth formulae, such as those salts with inorganic acids such as, for example, hydrochloric, hydrobromic, sulphuric, phosphoric acids and the like and with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acids and the like.

Illustrative compounds according to the invention include 2-[(diphenylmethyl)imino]piperidine-3-carboxanilide, 2-[(1,1-diphenylethyl)imino]piperidine-3-carboxanilide, 2-[(1,1-diphenylpropyl)imino]piperidine-3-carboxanilide, 2-[(1,1-diphenylbutyl)imino]piperidine-3-carboxanilide, 2-[(1,1-diphenylpentyl)imino]piperidine-3-carboxanilide, 2-[(2,2-diphenylethyl)imino]piperidine-3-carboxanilide and 2-[(2,2-diphenylpropyl)imino]piperidine-3-carboxanilide. Also included are compounds where the methylene group in the last-named compound is replaced by an ethylene, a propylene and a butylene group, as well as each of the foregoing, wherein the methyl group on the benzhydryl carbon is replaced by an ethyl, propyl or butyl group.

Additional compounds of this invention include the p-fluoro substituted carboxanilide analog of each of the above-named compounds. Other examples are the o-fluoro and m-fluoro isomers of each of the foregoing compounds, and the analogous compounds having a chlorine or bromine atom, a methyl group, a methoxy or methylthio group, a trifluoromethyl group, a trifluoromethoxy group, or a trifluoromethylthio group in place of the fluorine atom of each of the above compounds.

Still further specific illustrations of the compounds of the invention are the monofluoro-substituted and difluoro-substituted compounds having a fluorine atom at the para-position of one or both benzene rings of the benzhydryl moiety of each of the first-named compounds set forth above. Other specific examples are the ortho-fluoro and the meta-fluoro compounds otherwise corresponding to each of the foregoing. The compounds analogous to the foregoing with a chlorine or bromine atom, a methyl group, a methoxy group, a thiomethyl group, a trifluoromethyl group, a trifluoromethoxy group, or a trifluoromethylthio group are further specific examples of compounds of this invention.

Still further specific examples of the compounds of the invention are the 3,5-dichlorocarboxanilides and the 2,4,6-trimethylcarboxanilides corresponding to each of the unsubstituted compounds named hereinabove. Other examples are the 2,3-substituted, 2,4-substituted, 2,5-substituted, 2,6-substituted and 3,4-substituted carboxanilides isomeric with the foregoing 3,5-dichlorocarboxanilides and the 2,3,4-substituted, 2,3,5-substituted, 2,3,6-substituted, 2,4,5-substituted and 3,4,5-substituted trimethylcarboxanilides corresponding to the 2,4,6-trimethylcarboxanilides named hereinabove.

Analogous disubstituted compounds having in place of each of the chlorine atoms a fluorine or bromine atom, a methyl or methoxy group, a methylthio group, a trifluoromethyl, trifluoromethoxy or trifluoromethylthio group, further illustrate compounds of this invention. Analogous compounds having a fluorine, chlorine or bromine atom, an alkoxy or alkylthio group, a trifluoromethyl group, a trifluoromethoxy group, or a trifluoromethylthio group in place of each of the three methyl groups in the 2,4,6-trimethylcarboxanilides named above are also illustrative.

Further illustrative compounds of the invention are those wherein either one or both benzhydryl aromatic rings bears two or three substituents substituted in a fashion entirely analogous to the substitution patterns of the above-named disubstituted and trisubstituted carboxanilides. Those compounds wherein the phenyl group of the carboxanilide moiety is mono-substituted, disubstituted and tri-substituted as shown above are additional illustrative compounds.

As used herein, the term gastrointestinal hypersecretion is intended to mean hypersecretion of fluid in the small intestine and hypersecretion of fluid in the stomach or gut, particularly hydrochloric acid and pepsin, collectively referred to as gastric fluid hypersecretion. The compounds of Formula I are useful in the treatment of gastrointestinal ulcers, that is, ulcers of the gut and duodenum, and diarrhea mediated by enterotoxins, such as, Vibrio, cholera, Escherichia coli, Shigella species, Salmonella, Clostridium, and Klebsiella species, diarrhea mediated by a viral agent, such as, orbivirus, and also, diarrhea resulting from administration of antibiotics. The compounds may be administered to warm blooded animals including mammals, such as dogs, cats, rats, horses, bovine cows, mice, pigs, goats, sheep and humans and birds, such as, chickens and turkeys.

The compounds may be administered alone or may be used in combination with antibiotics, such as, antibacterial agents, for example, clindamycin, lincomycin, tetracycline and cephalosporins used in general therapy or for the treatment of the enterotoxins. The compounds may also be used with other antisecretory agents, such as, diphenoxylate and atropine, and with electrolyte solutions serving as fluid replacement or maintenance therapy. The compounds may be administered alone or in the form of pharmaceutical preparations and may be administered orally or parenterally, for example, intravenously and intraperitoneally. Pharmaceutical preparations containing conventional pharmaceutical carriers and, as active ingredients, compounds of Formula I can be employed in unit dosage forms, such as solids, e.g., tablets, capsules and pills, or liquid solutions, suspensions and emulsions for oral and parenteral administration.

The amount of compound administered can be any gastrointestinal hypersecretion inhibitory effective amount, or any gastric or intestinal hypersecretion inhibitory effective amount, which amounts would be effective in treating ulcers or diarrhea, that is, an antiulcer or anti-diarrheal effective amount. The dosage unit administered can vary over a wide range to provide from about 0.1 mg/kg (milligram per kilogram) to about 250 mg/kg of body weight of the patient per day, and preferably from about 1 mg/kg to about 100 mg/kg of body weight of the patient per day to achieve the desired effect. Unit doses may contain from about 5 mg to about 500 mg of the compound and may be administered, for example, from 1 to 4 times daily. In addition, the compounds may also be administered on alternate days or series of days and may be administered alone or concurrently, sequentially or serially with other agents as mentioned above. As used herein, the term patient is intended to mean the animal or mammal being treated. Illustrative examples of suitable pharmaceutical preparations of the compounds of Formula I are set forth hereinbelow.

The compounds of the present invention, having the Formula I, are conveniently prepared by reacting O-methylvalerolactim-3-carboxanilides (IV) with diphenylalkylamines (V), as shown in Scheme 1.

Scheme 1

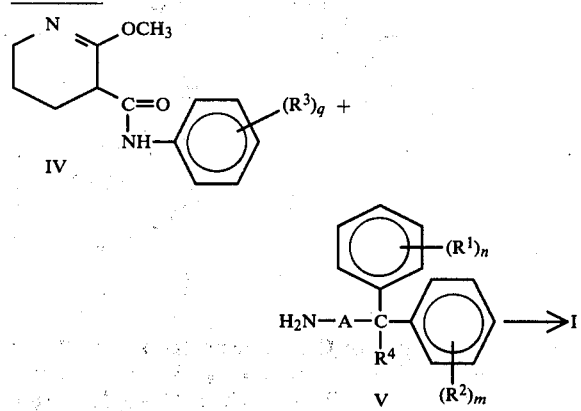

In the above Scheme, $R^1$, $R^2$, $R^3$, $R^4$, A, n, m and q are as defined hereinabove. This general type of reaction is reported by Benson et al, J. Am. Chem. Soc., 70, 2115 (1948); and exemplified in related compounds by Grisar et al, J. Med. Chem., 16, 885 (1973) and in U.S. Pat. Nos. 3,783,162, 3,963,701 and 4,061,746. The reaction may be carried out in the presence or the absence of a solvent, although the use of a solvent is preferred. Suitable solvents include aliphatic hydrocarbons such as petroleum ethers, aromatics such as benzene, toluene, or xylene, chlorinated hydrocarbons such as carbon tetrachloride, ethylene dichloride, methylene chloride or chloroform, chlorinated aromatics such as 1,2,4-trichlorobenzene or o-dichlorobenzene, ethereal solvents such as diethyl ether, tetrahydrofuran, or p-dioxane, or preferably alcohols such as ethanol, propanol or most preferably methanol. The reaction is effected at a temperature of from 0° to 100° C., preferably about 25° C., for from 1 hour to 20 days, preferably about 5–10 days. The ratio of imine ether IV to amine V is desirably from about 10:1 to about 1:10, preferably about 1:1. A catalyst may be used to facilitate the reaction, in an amount of from about 0.001 to about 1 equivalent. Suitable catalysts include anhydrous mineral acids such as dry HCl, alkanoic acids such as acetic acid, or sulfonic acids such as methanesulfonic acid or p-toluenesulfonic acid. Alternatively, the hydrochloride salt of the amine V is used as reactant and catalyst. The reactants are generally combined with the solvent and allowed to stand until reaction is complete. The mixture is then cooled and the resultant solid is collected, washed with a little solvent and recrystallized to give the purified product of Formula I or a salt thereof.

The O-methylvalerolactim-3-carboxanilides IV are prepared by reacting O-methylvalerolactim (VI) with a phenylisocyanate (VII), as shown in Scheme 2. This reaction is reported in an article by Kraatz, *Tetrahedron*, 29, 3991 (1973).

Scheme 2

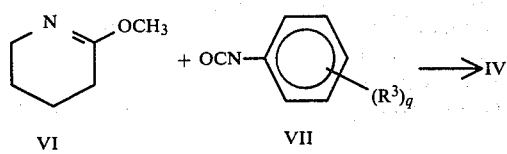

In the above Scheme, $R^3$ and q are as defined hereinabove. O-methylvalerolactim (VI) may be prepared from the commercially available valerolactam by methods known in the art. For example, by the reaction of valerolactam with dimethyl sulfate in a solvent such as benzene, toluene or xylene at the reflux temperature of the solvent for from 2 to 24 hours, the corresponding O-methylvalerolactim is obtained. The phenylisocyanates (VII) are either commercially available or readily obtained by Curtius rearrangement of acyl azides derived from the corresponding benzoic acids.

The reaction of Scheme 2 is carried out either in the presence or the absence of a solvent, preferably in the absence of solvent. However, the reaction may be effected in aliphatic hydrocarbons such as petroleum ethers, aromatics such as benzene, toluene or xylene, chlorinated hydrocarbons such as carbon tetrachloride, ethylene chloride, methylene chloride, chloroform, chlorinated aromatics such as 1,2,4-trichlorobenzene or o-dichlorobenzene, or ethers such as diethyl ether, tetrahydrofuran or p-dioxane. The reaction is effected at a temperature of from 0° to 100° C., preferably about 25° C., for from 1 to 20 days, preferably about 5–10 days. The reactants are combined in a ratio of VI:VII of from 10:1 to 1:10, preferably about 1:1. After standing for a time sufficient to effect reaction, the resultant prodct, generally in the form of a crystalline mass, is recrystallized from an appropriate solvent, such as benzene, hexane or mixtures thereof.

The diphenylalkylamines V are prepared by a variety of synthetic pathways. Simple benzhydrylamines are prepared by first reacting a phenyl Grignard reagent with a benzonitrile, and reducing the intermediate imine or its salt with, for example, lithium aluminum hydride, as shown in Scheme 3, and reported by Grisar et al, *J. Med. Chem.*, 16, 885 (1973).

Scheme 3

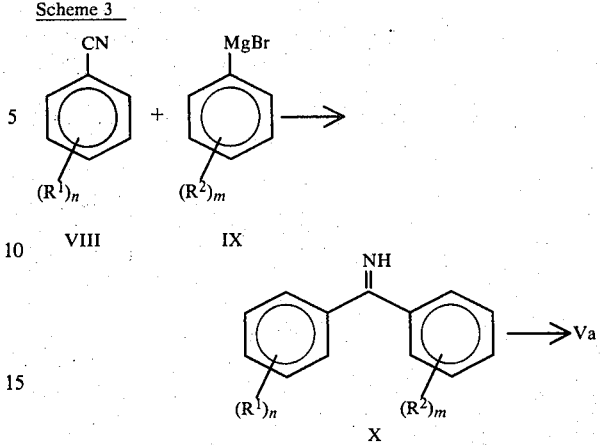

In the compounds of Scheme 3, $R^1$, $R^2$, n and m are as defined hereinabove. In the benzhydrylamine products obtained according to this Scheme, Va, A is a bond and $R^4$ is H. The phenyl Grignard reagent IX is prepared in a conventional manner, normally in an ether solution, and treated with an ethereal solution of the benzonitrile VIII. The reaction may be refluxed and/or allowed to stand for a time sufficient to effect reaction, and the reaction mixture is then added to a stirred suspension of lithium aluminum hydride in anhydrous ether. The mixture is refluxed for a sufficient time to effect reaction, decomposed by addition of water, and optionally base, and the resultant amine precipitated from the ether phase, preferably as its hydrochloride salt, which is then recrystallized from an appropriate solvent.

The intermediate imine X produced by the reaction of Scheme 3 may be hydrolyzed with aqueous acid to produce benzophenones having the Formula XI, as shown in Scheme 4, wherein $R^1$, $R^2$, n and m are as defined hereinabove. The formula for these benzophenones is abbreviated, as shown below, as $Ar_2C=O$.

Scheme 4

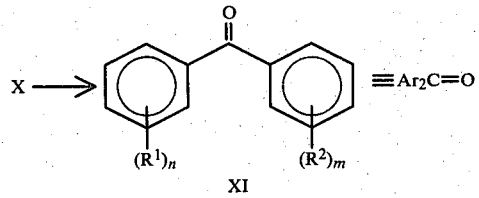

Further transformations of benzophenones XI are shown in Scheme 5.

Scheme 5

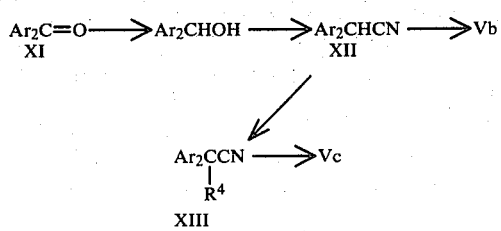

The benzophenones XI obtained by the process of Scheme 4 may be reduced to benzhydryl alcohols, for example, with sodium borohydride or lithium aluminum hydride. These in turn may be converted to their sulfonate esters, e.g., toluenesulfonates or methanesulfonats, or to benzhydryl halides. The halides or sulfonates may be displaced with cyanide to form diphenylacetonitriles XII, which may be reduced either by catalytic hydrogenation or with lithium aluminum hydride to the corresponding 2,2-diarylethylamines Vb. Alternatively, the diphenylacetonitriles XII may be alkylated in the presence of strong base, e.g., sodium amide or potassium tert-butoxide, to produce α-alkyldiarylacetonitriles XIII, which can be reduced as above to produce the corresponding alkyldiarylethylamines Vc. An example of this reaction is reported by Schultz et al, *J. Am. Chem. Soc.*, 69, 2454 (1947), who describe the production of 2,2-diphenylpentanenitrile (Vc, $R^4$=n-propyl).

Higher homologs of amines Vb and Vc may be prepared by a conventional sequence shown in Scheme 6, which illustrates the sequence beginning with α-alkyldiarylacetonitriles XIII.

Scheme 6

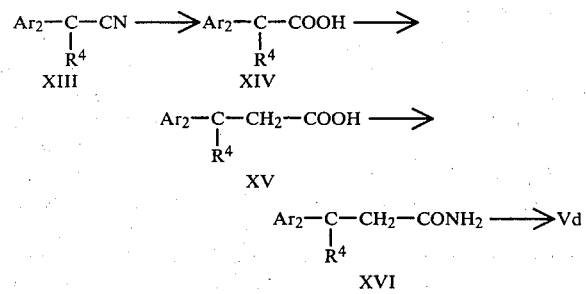

In the above scheme, Ar and $R^4$ are as defined hereinabove. The α-alkyldiarylacetonitriles XIII are hydrolyzed to the corresponding carboxylic acids XIV, which may be homologated using the Arndt-Eistert synthesis, as described in March, *Advanced Organic Chemistry: Reactions, Mechanisms, and Structure*, pages 809–810 (McGraw-Hill, New York, 1968), to give the next higher acid XV, which may be converted to the corresponding amide XVI, which in turn may be reduced, e.g., with lithium aluminum hydride or by catalytic hydrogenation, to the homologous, β-alkyldiarylpropylamines Vd. The acids XV may be further homologated to produce the higher homologs which can also be converted to amines corresponding to Formula I. These higher homologs may also be produced by alternative syntheses by pathways known to those skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

O-Methylvalerolactim-3-carboxanilide (IV, q=O)

A mixture of 11.3 g (0.1 mol) of O-methylvalerolactim, produced by the method of Benson et al, loc. cit., and 11.9 g (0.1 mol) of phenylisocyanate (Eastman) is allowed to stand at room temperature for three days. The resultant product is recrystallized from benzene to give the purified product, m.p. 129°–131° C.

The above procedure is repeated, with the phenylisocyanate replaced by the substituted phenylisocyanates shown below to give the corresponding substituted lactim ether carboxanilides, as shown in the following table.

| VII, $R^3$(q = 1) | m.p. |
|---|---|
| p-CH$_3$ | 158–161° C. |
| p-OCH$_3$ | 147–150° C. |
| p-Cl | 117–121° C. |

EXAMPLE 2

2-[(Diphenylmethyl)imino]piperidine-3-carboxanilide hydrochloride (I, A=bond, n=m=q=0)

A mixture of 9.5 g (0.041 mol) of O-methylvalerolactim-3-carboxanilide and 9.0 g (0.041 mol) of benzhydrylamine hydrochloride is treated with a few mls of anhydrous ethanol and thoroughly mixed to form a paste. After standing at room temperature for 48 hours, the paste is treated with ether, cooled, and the resultant semisolid product is separated from the supernatent. Recrystallization from methanol/acetone yielded the pure product, m.p. 243°–245° C. (dec.).

EXAMPLE 3

2-[(2,2-Diphenylpentyl)imino]piperidine-3-carboxanilide hydrochloride (I, A=CH$_2$, n=m=q=O, $R^4$=C$_3$H$_7$)

A mixture of 11.6 g (0.05 mol) of O-methylvalerolactim-3-carboxanilide and 13.8 g (0.05 mol) of 2,2-diphenylpentylamine hydrochloride in 50 ml of dry methanol is allowed to stand at room temperature for seven days. The methanol is removed from the resultant homogeneous mixture by aziotropic distillation with acetone. Addition of a small amount of isopropanol to the resultant solution produces a crystalline produuct, which is isolated and recrystallized from isopropanol/ether to give the pure product, m.p. 224°–228° C. (dec.).

When the substituted O-methylvalerolactim-3-carboxanilides prepared in Example 1 are used in place of O-methylvalerolactim-3-carboxanilide, the analogous substituted products are obtained, as the hydrochlorides, as shown in the following table.

| I, A = CH$_2$, $R^4$ = C$_3$H$_7$ $R^3$(q = 1) | m.p. (recryst. solvent) |
|---|---|
| p-CH$_3$ | 225–227° C., dec. (i-PrOH) |
| p-OCH$_3$ | 140–142° C., dec. (MeOH/acetone) |
| p-Cl | 212–214° C., dec. (i-PrOH) |

EXAMPLE 4

| Tablets | mg/tablet |
|---|---|
| (a) 2-[(Diphenylmethyl)imino]piperidine-3-carboxanilide hydrochloride | 15 |
| (b) Lactose | 33 |
| (c) Corn starch | 11.25 |
| (d) Sucrose 3% starch | 12.75 |
| (e) Corn starch paste (10%) | 1.50 |
| (f) Zinc Stearate | 1.50 |

The dry lactose, corn starch and sucrose 3% starch are screened through a 30-mesh screen and blended. The powder mix is granulated with 10% corn starch paste, and the wet granulation is passed through a No. 4 screen and dried. The dried granulation is screened and blended with the zinc stearate which also is screened, and the resulting mixture is compressed into tablets weighing 75 mg each.

An enteric coated tablet is afforded when a tablet formulated as above is sprayed with a 4% solution of hydroxypropyl methylcellulose phthalate, increasing the weight of the tablet about 6 mg.

EXAMPLE 5

| Injectable Solution | Grams |
|---|---|
| (a) 2-[(2,2-Diphenylpentyl)imino]piperidine-3-carboxanilide hydrochloride | 1 |
| (b) Polyethylene glycol 4000, U.S.P. (Av. mol. wt. 4,000) | 3 |
| (c) Sodium chloride | 0.9 |
| (d) Polyoxyethylene derivatives of sorbitan monooleate (TWEEN 80) U.S.P. | 0.4 |
| (e) Sodium metabisulfite | 0.1 |
| (f) Methylparaben, U.S.P. | 0.18 |
| (g) Propylparaben, U.S.P. | 0.02 |
| (h) Water for injection to make 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and the polyoxyethylene derivatives of sorbitan monooleate. The cooled solution is adjusted to the final volume with water for injection and is then sterilized by sterile filtration through a suitable filter. Each 1 ml of solution contains 10 mg of the active ingredient.

EXAMPLE 6

| Capsule | Grams |
|---|---|
| (a) 2-[(2,2-Diphenylpentyl)imino]piperidine-3-(4-chlorocarboxanilide)-hydrochloride | 100 |
| (b) Lactose, U.S.P. | 100 |
| (c) Starch, U.S.P. | 10 |
| (d) Talc, U.S.P. | 5 |
| (e) Calcium stearate | 1 |

The finely powdered materials are mixed until uniformly dispersed and filtered into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

The preceding examples can be repeated with similar success by substituting the generically or specifically described reactants and/or operating conditions of this invention for those use in the preceding examples.

From the foregoing description, one skilled in the art can easily ascertain the essential characteristics of this invention, and without departing from the spirit and scope thereof, can make various changes and modifications of the invention to adapt it to various usage and conditions.

What is claimed is:

1. A compound of the formula

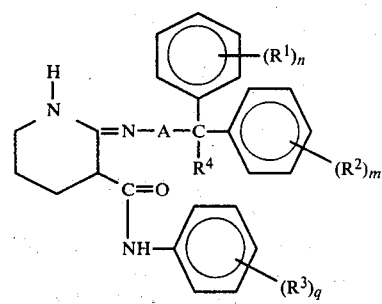

wherein A is a bond or $C_{1-4}$ alkylene; $R^1$, $R^2$ and $R^3$ are independently a halogen atom, $C_{1-4}$ alkyl, $C_{1-4}$ alkoxy, $C_{1-4}$ alkylthio, $CF_3$, $SCF_3$ or $OCF_3$; $R^4$ is a hydrogen atom or $C_{1-4}$ alkyl; and n, m and q are independently an integer from 0 to 3; or a pharmaceutically acceptable acid addition salt thereof.

2. A compound of claim 1, wherein q is 1 and $R^3$ is o-$OCH_3$ or m-$CF_3$.

3. A compound of claim 1, wherein $R^4$ is $CH_3$.

4. A compound of claim 1, wherein A is $CH_2$ and $R^4$ is H.

5. A compound of claim 1, wherein n and m are each 1, and $R^1$ and $R^2$ independently are each Cl or $CF_3$.

6. A compound of claim 1, wherein A is $CH_2$ and $R^4$ is $C_3H_7$.

7. The compound of claim 1, which is 2-[(diphenylmethyl)imino]piperidine-3-carboxanilide or a pharmaceutically acceptable acid addition salt thereof.

8. The compound of claim 1, which is 2-[(2,2-diphenylpentyl)imino]piperidine-3-carboxanilide or a pharmaceutically acceptable acid addition salt thereof.

9. The compound of claim 1, which is 2-[(2,2-diphenylpentyl)imino]piperidine-3-(4-methylcarboxanilide) or a pharmaceutically acceptable acid addition salt thereof.

10. The compound of claim 1, which is 2-[(2,2-diphenylpentyl)imino]piperidine-3-(4-methoxycarboxanilide) or a pharmaceutically acceptable acid addition salts thereof.

11. The compound of claim 1, which is 2-[(2,2-diphenylpentyl)imino]piperidine-3-(4-chlorocarboxanilide) or a pharmaceutically acceptable acid addition salt thereof.

12. The compound of claim 1, which is 2-[(2,2-diphenylpentyl)imino]piperidine-3-(3-trifluoromethylcarboxanilide) or a pharmaceutically acceptable acid addition salt thereof.

13. A method of treating gastrointestinal hypersecretion in a patient suffering from the symptoms thereof, which comprises administering to said patient an amount effective for inhibiting gastrointestinal hypersecretion of a compound of the formula

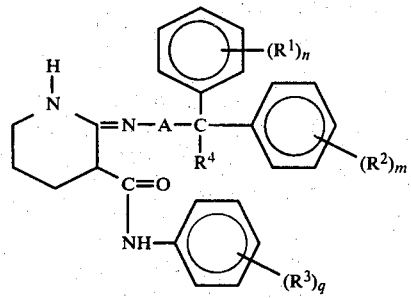

wherein A is a bond or $C_{1-4}$ alkylene; $R^1$, $R^2$ and $R^3$ are independently a halogen atom, $C_{1-4}$ alkyl, $C_{1-4}$ alkoxy, $C_{1-4}$ alkylthio, $CF_3$, $SCF_3$ or $OCF_3$; $R^4$ is a hydrogen atom or $C_{1-4}$ alkyl; and n, m and q are independently an integer from 0 to 3; or a pharmaceutically acceptable acid addition salt thereof.

14. The method of claim 13, wherein q is 1 and $R^3$ is o-$OCH_3$ or m-$CF_3$.

15. The method of claim 13, wherein $R^4$ is $CH_3$.

16. The method of claim 13, wherein A is $CH_2$ and $R^4$ is H.

17. The method of claim 13, wherein n and m are each 1, and $R^1$ and $R^2$ independently are each Cl or $CF_3$.

18. The method of claim 13, wherein A is $CH_2$ and $R^4$ is $C_3H_7$.

19. The method of claim 13, wherein the compound is 2-[(diphenylmethyl)imino]piperidine-3-carboxanilide or a pharmaceutically acceptable acid addition salt thereof.

20. The method of claim 13, wherein the compound is 2-[2,2-diphenylpentyl)imino]piperidine-3-carboxanilide or a pharmaceutically acceptable acid addition salt thereof.

21. The method of claim 13, wherein the compound is 2-[(2,2-diphenylpentyl)imino]piperidine-3-(4-methylcarboxanilide) or a pharmaceutically acceptable acid addition salt thereof.

22. The method of claim 13, wherein the compound is 2-[2,2-diphenylpentyl)imino]piperidine-3-(4-methoxycarboxanilide) or a pharmaceutically acceptable acid addition salt thereof.

23. The method of claim 13, wherein the compound is 2-[(2,2-diphenylpentyl)imino]piperidine-3-(4-chlorocarboxanilide) or a pharmaceutically acceptable acid addition salt thereof.

24. The method of claim 13, wherein the compound is 2-[(2,2-diphenylpentyl)imino]piperidine-3-(3-trifluoromethylcarboxanilide) or a pharmaceutically acceptable acid addition salt thereof.

25. The method of claim 13, wherein said amount is from about 0.1 mg/kg to about 250 mg/kg of body weight of the patient per day.

26. The method of claim 25, wherein said amount is from about 1 mg/kg to about 100 mg/kg per day.

27. A pharmaceutical composition for the treatment of gastrointestinal hypersecretion, which comprises a gastrointestinal hypersecretion inhibitory amount of a compound of the formula

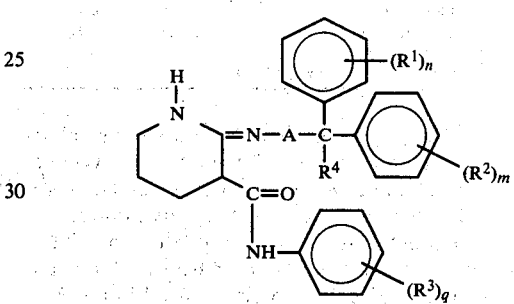

wherein A is a bond or $C_{1-4}$ alkylene; $R^1$, $R^2$ and $R^3$ are independently a halogen atom, $C_{1-4}$ alkyl, $C_{1-4}$ alkoxy, $C_{1-4}$ alkylthio, $CF_3$, $SCF_3$ or $OCF_3$; $R^4$ is a hydrogen atom or $C_{1-4}$ alkyl; and n, m and q are independently an integer from 0 to 3; or a pharmaceutically acceptable acid addition salt thereof;

and a pharmaceutically acceptable carrier.

* * * * *